(12) United States Patent
Jackson et al.

(10) Patent No.: US 8,808,645 B2
(45) Date of Patent: Aug. 19, 2014

(54) MOLECULAR FILTERS

(75) Inventors: Warren Jackson, San Francisco, CA (US); Zhiyong Li, Foster City, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 29 days.

(21) Appl. No.: 13/281,232

(22) Filed: Oct. 25, 2011

(65) Prior Publication Data
US 2013/0100436 A1 Apr. 25, 2013

(51) Int. Cl.
*B01D 35/00* (2006.01)
*B01D 41/00* (2006.01)
*B01D 63/00* (2006.01)
*C02F 1/44* (2006.01)
*B01D 24/00* (2006.01)
*B01D 39/00* (2006.01)
*B01D 61/42* (2006.01)
*A61M 37/00* (2006.01)

(52) U.S. Cl.
USPC ............ 422/534; 210/321.74; 210/321.83; 210/488; 210/490; 210/497.1; 210/321.78; 210/504; 204/640; 604/6.09

(58) Field of Classification Search
None
See application file for complete search history.

(56) References Cited

U.S. PATENT DOCUMENTS 7,279,096 B2 * 10/2007 Murray .................. 210/500.34
7,393,687 B2   7/2008 Geltser
2004/0191246 A1 * 9/2004 Connelly et al. ............ 424/140.1
2006/0146323 A1 * 7/2006 Bratkovski et al. ............ 356/301
2007/0062857 A1 * 3/2007 Popa et al. ................ 210/321.83
2007/0128423 A1   6/2007 Belfort et al.
2008/0071352 A1 * 3/2008 Weber et al. ................. 623/1.15
2008/0241185 A1 * 10/2008 Kofinas et al. ............. 424/204.1
2010/0068242 A1 * 3/2010 Cantrell et al. ............... 424/423
2010/0166654 A1   7/2010 Safavy
2010/0226984 A1   9/2010 Zhou
2010/0268199 A1 * 10/2010 Hyde et al. ................. 604/891.1

FOREIGN PATENT DOCUMENTS

WO   WO-2007020642   2/2007

OTHER PUBLICATIONS

Alexander et al., Molecular Imprinting science and technology: a survey of the literature for the years up to and including 2003, Jan. 4, 2006, Journal of Molecular Recogntion, vol. 19, pp. 106-180.*
Cai, D. et al., A Molecular-imprint Nanosensor for Ultrasensitive Detection of Proteins, (Research Paper), Nature Nanotechnology, Jun. 27, 2010, pp. 597-601, vol. 5, Macmillan.

* cited by examiner

*Primary Examiner* — Jill Warden
*Assistant Examiner* — Julie Tavares

(57) ABSTRACT

Molecular filters are disclosed herein. An example of the molecular filter includes a rolled substrate having an interior surface and opposed ends that are substantially orthogonal to the interior surface. The rolled substrate defines a layer and a fluid flow path extending from one of the opposed ends to another of the opposed ends. A template is positioned on the interior surface of the rolled substrate. The template includes a matrix, and molecule template locations formed in the matrix.

17 Claims, 5 Drawing Sheets

MOLECULAR FILTERS

BACKGROUND

The present disclosure relates generally to molecular filters.

Assays and other sensing systems have been used in the chemical, biochemical, medical and environmental fields to detect the presence and/or concentration of one or more chemical substances. Some sensing techniques utilize color or contrast for substance detection and measurement, for example, those techniques based upon reflectance, transmittance, fluorescence, or phosphorescence. Other sensing techniques, such as Raman spectroscopy or surface enhanced Raman spectroscopy (SERS), study vibrational, rotational, and other low-frequency modes in a system. When performing any of these sensing techniques, it may be desirable to filter out or collect certain molecules (e.g., analytes of interest) from a fluid for analysis, while allowing other molecules in the fluid to pass. Filters are often based upon the cross-sectional area of the molecules. As such, larger molecules are filtered out, while smaller molecules are allowed to pass through the filter.

BRIEF DESCRIPTION OF THE DRAWINGS

Features and advantages of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

DETAILED DESCRIPTION

Examples of the molecular filter disclosed herein have a three-dimensional volume for collecting molecules for electrical and/or optical analysis. More particularly, the molecular filter(s) disclosed herein include a rolled substrate that includes a template for capturing one or more types of molecules from a fluid that is directed through the rolled substrate. The template is designed to remove molecule(s) based on shape and function, rather than by cross-sectional area. As such, the molecular filter may be customized for one or more particular species. Additionally, the three-dimensional volume provides (e.g., when compared to a planar two-dimensional volume) an increase in the surface area for the introduced fluid to interact, an increase in the probability of capturing the species of interest, and a more dynamic (e.g., different and/or faster) diffusion mechanism. The three-dimensional volume of examples of the molecular filter may also provide desirable sensitivity and throughput.

The molecular filter(s) disclosed herein may be used in a variety of applications to filter molecule(s) from a variety of liquids or gases. As examples, the filters disclosed herein may be used as a body fluid filter, a water filter, an air filter (e.g., in air quality monitoring applications), or the like.

Figure 1A:
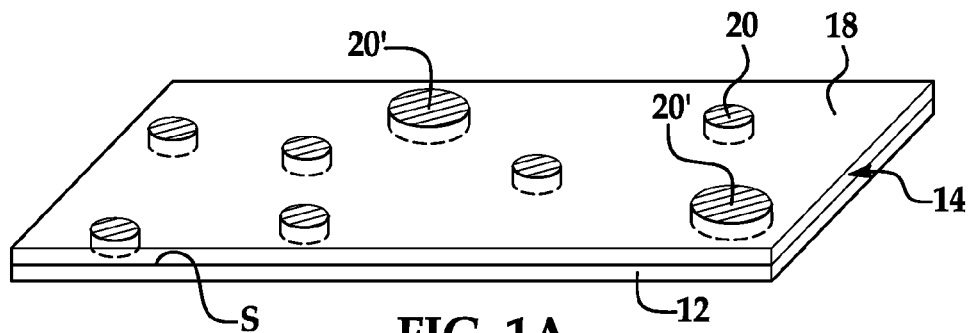
FIGS. 1A through 1C are perspective views that together illustrate the formation of an example of a molecular filter.
Figure 1B:
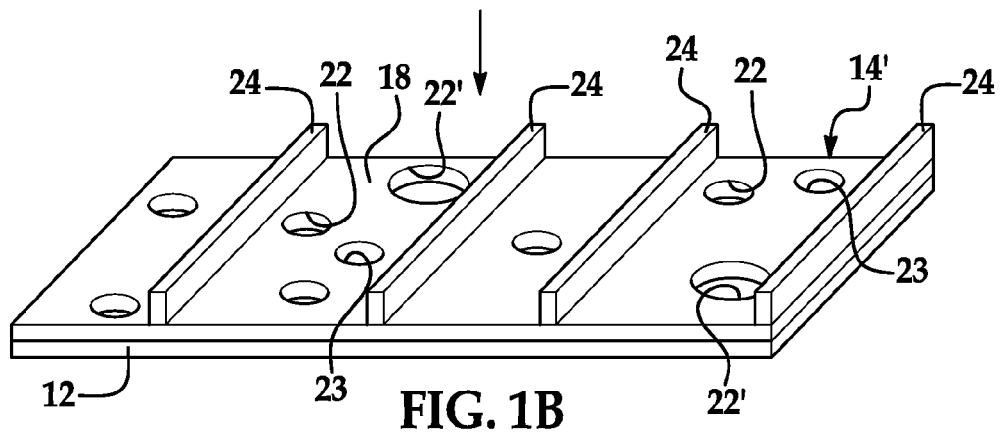
Figure 1C:
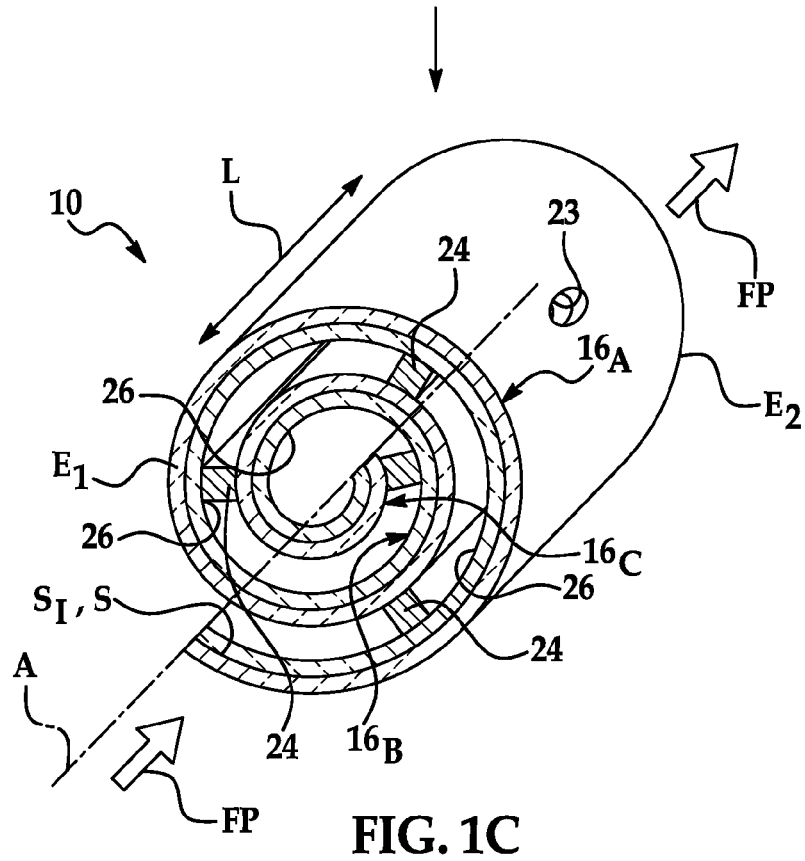

Referring now to FIGS. 1A through 1C, an example method for forming an example molecular filter 10 is depicted. FIG. 1A illustrates a substrate 12 and a pre-template 14 formed on the substrate 12. The material and thickness used for the substrate 12 enable the substrate 12 to be rolled to form a plurality of layers 16 (shown in FIG. 1C). Suitable substrate materials include polymers (e.g., polyimide, poly(ethylene terephthalate) (PET), poly(ethylene 2,6-naphthalate) (PEN), stainless steel, silk fibrin, biocompatible silicate-collagen hybrid fibril sheets, biocompatible silicone rubber based on poly(methylhydrogensiloxane-co-dimethylsiloxane), graphene oxide-based sheets, bio-functionalized graphene, and substrates with patterned cell signaling proteins. When the molecular filter 10 is to be used in an optical sensing system (see system 100' in FIG. 7), an optically transmissive substrate may be selected. The thickness of the substrate 12 ranges from about 2 µm to about 250 µm. The length and/or width of the substrate 12 may be any desirable dimensions, depending, at least in part, on the desirable surface area of the final molecular filter 10.

The pre-template 14 is a precursor to the template 14' that will be formed. The pre-template 14 includes a matrix 18 and one or more types of template molecules 20. The pre-template 14 has a thickness ranging from about 1 nm to about 10 µm. Due, at least in part, to the thickness of the pre-template 14 and the size of the template molecules 20, the template molecules 20 are present at the surface of the pre-template 14.

Figure 2A:
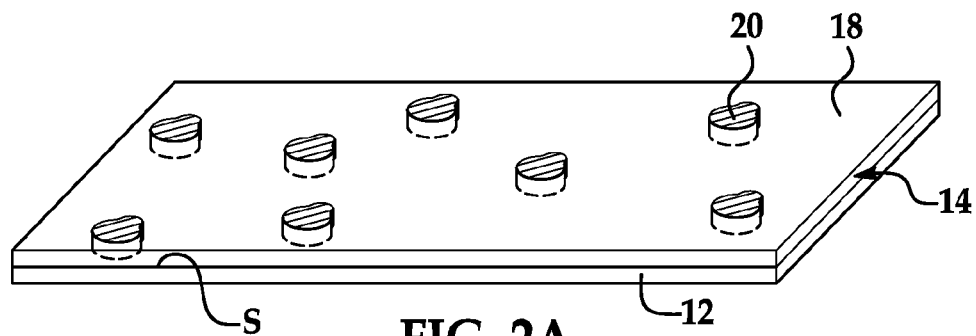
FIGS. 2A through 2C are perspective views that together illustrate the formation of another example of a molecular filter.

The template molecules 20 are selected based upon the desired molecule(s) that is/are to be filtered/captured using the molecular filter 10. Some examples include trinitrotoluene for explosive detection applications, antibodies to filter/detect the antigens in a body fluid, etc. A single type of template molecule 20 may be selected, or a variety of different template molecules 20 (and 20' shown in FIG. 3A) may be selected. FIG. 1A illustrates two different template molecules 20, 20' scattered throughout the same matrix 18, and FIG. 2A illustrates the same template molecule 20 scattered throughout the matrix 18. It is to be understood that when multiple different template molecules 20 (and 20') are selected, they may be present in the same matrix 18 (FIG. 1A), or they may be included in different matrices 18, 18' (shown and discussed in reference to FIG. 3A). When different template molecules 20 are included in the same matrix 18, the template molecules 20 may be mixed throughout the matrix 18. This mixture may be used to form a template 14' having different molecule template locations (which are labeled 22, 22') across the surface of the template 14' and along the length L (FIG. 1C) of the filter 10. As mentioned above, different template molecules 20, 20' included in different matrices 18, 18' are shown and discussed further in reference to FIG. 3A. In the examples disclosed herein, the template molecules 20 (and 20') desirably create molecule template locations 22 (and 22') within the matrix 18 (and/or 18') which have unique shapes that selectively bind to target molecule class(es) within a solution that is filtered, rather than binding to the solution or other non-target molecules that may be present in the solution.

The matrix 18 may be a polymer matrix or a host molecule matrix. When a polymer matrix is used, the template molecules 20, 20' may be mixed into the polymer selected as the matrix 18, and this mixture may be coated on the surface S of the substrate 12 to form the pre-template 14. The polymer matrix/template molecule mixture may be coated on the surface S using gravure coating, spin coating, dropping cast, spraying, or the like. Examples of suitable polymer matrix materials include polyacrylate, polysiloxane, expoxy polymer, or the like.

When a host molecule matrix is used, the matrix 18 is made up of a plurality of host molecules. When in the presence of particular analyte(s) (i.e., guest molecule(s)), the host molecule matrix is able to form complexes with the guest molecule(s), where the complexes are held together by forces other than those of full covalent bond. Therefore, the host molecule matrix involves host-guest chemistry, which encompasses the notion of molecular recognition and interactions through non-covalent bonding. The host molecule selected for the host molecule matrix will depend, at least in part, on the desired guest molecule(s) to be filtered. Examples of suitable host molecules include cyclodextrins, calixarenes, cucurbiturils, porphyrins, metallacrowns, crown ethers, zeolites, cyclotriveratrylenes, cryptophanes and carcerands. When a host molecule matrix is used, the template molecules 20, 20' and host molecules may be mixed into a suitable solvent, and this solution may be coated on the surface S of the substrate 12. The solvent evaporates, leaving behind the pre-template 14 including the template molecules 20, 20' in the matrix 18.

When the resulting filter 10 is to be used with optical sensing techniques, it may be desirable that the matrix 18 be an optically transparent material. The optical transparency may depend upon the sensing technique to be formed, for example, the matrix 18 may be optically transparent to visible and/or near-infrared wavelengths when Raman spectroscopy or surface enhanced Raman spectroscopy is to be performed.

After the pre-template 14 is formed, the template molecules 20 are removed from the pre-template 14 to form the template 14', as shown in FIG. 1B. The method utilized to remove the template molecules 20, 20' may depend, at least in part, on the template molecules 20, 20' used and the matrix 18 used. It is desirable to remove the template molecules 20, 20' without deleteriously affecting the matrix 18 or the molecule impression that will be left in the matrix 18. The removal of the template molecules 20, 20' may be initiated or achieved by chemical, thermal, electrical, and/or optical means. As an example, chemical removal may be accomplished by exposing the template molecules 20, 20' to a solvent. It is to be understood that the solvent selected should also be a non-solvent of the matrix 18 so that while the template molecules 20, 20' are dissolved, the matrix 18 remains intact.

As another example, the template molecules 20, 20' may be removed by decomposition. The decomposition of the template molecules 20, 20' may be induced chemically, thermally, electrically, and/or optically. Inducing decomposition chemically may be accomplished by exposing the template molecules 20, 20' to a suitable acid or base. Inducing decomposition thermally may be accomplished by heating the template molecules 20, 20'. Inducing decomposition electrically may be accomplished by applying a bias that will initiate a redox process to decompose the template molecules 20, 20'. Application of the bias may be accomplished using the substrate 12 if it is conductive or using an electrode that is incorporated into the device 10. Inducing decomposition optically may be accomplished by exposing the template molecules 20, 20' to ultraviolet (UV) light, which will initiate a photochemical reaction to decompose the template molecules 20, 20'.

The removal of the template molecules 20, 20' from the matrix 18 forms molecule impressions, or molecule template locations 22, 22' in the matrix 18, and also forms the template 14'. The respective molecule template locations 22, 22' have the shape of the respective template molecules 20, 20' that previously resided in the locations 22, 22'. As such, the molecule template locations 22, 22' each have the appropriate shape to capture the desired molecule when introduced into the filter 10.

In some examples, holes 23 may be formed through the template 14' and the substrate 12. Any suitable technique for creating holes 23 may be used, such as selective etching or other techniques. These holes 23 may be formed so that fluid may flow radially (in addition to laterally) through the ultimately formed filter 10. Radial fluid flow may advantageously allow the introduced fluid to move to or between neighboring spaces (labeled 26 in FIG. 1C) to redistribute fluid flow as desired in particular applications.

As shown in FIG. 1B, spacers 24 may be formed on the surface of the template 14'. Spacers 24 may be desirable, for example, when the substrate 12 having the template 14' thereon is rolled to form multiple layers 16. More particularly, when the substrate 12 having the template 14' thereon is rolled to form multiple layers 16 (e.g., $16_A$, $16_B$, and $16_C$ as shown in FIG. 1C), the spacers 24 ensure that spaces 26 are formed between the various layers $16_A$, $16_B$, and $16_C$. The rolling of the substrate 12 and template 14' will be discussed further in reference to FIG. 1C. The spacers 24 may be formed of any suitable organic or inorganic material. Examples of spacer materials include resist materials (SU8), polyamide, polyacrylate, polycarbonate, poly(methyl methacrylate) (PMMA), oxides (e.g., silicon dioxide or metal oxides), metals (e.g., gold, platinum, etc.). In an example, the material selected for the spacer(s) 24 may be inert. The material selected for the spacer(s) 24 may also have suitable mechanical properties (e.g., strength) to separate the layers $16_A$, $16_B$, and $16_C$ from one another, and to define the spaces 26 when the substrate 12 having the template 14' thereon is rolled.

The spacer(s) 24 may be deposited via any suitable technique. As examples, the spacer(s) 24 may be formed using physical vapor deposition through a mask, printing, electroless deposition, or other like techniques. In an example, the spacer(s) 24 is/are deposited to extend along the length L (shown in FIG. 1C) of the formed molecular filter 10, and to have a width that ranges from about 0.1 μm to about 100 μm. The spacer(s) 24 may also be deposited in any desirable pattern as long as desirable (e.g., optimal) fluid flow through the filter 10 may be achieved. Any number of spacers 24 may be used, but it is desirable that the spacers 24 occupy equal to or less than 1% of the total surface area of the template 14' so as to not interfere with subsequently performed sensing. When multiple spacers 24 are used, the spacers 24 may be spaced apart along the template 14' surface so that when the substrate 12 and template 14' are rolled, the spacers 24 are desirably positioned throughout the filter 10 to ensure fluid flow through the filter 10.

As briefly mentioned, FIG. 1C illustrates the molecular filter 10 after the substrate 12 having the template 14' thereon is rolled up. Rolling may be accomplished manually or via an automated process. Once rolled, the molecular filter 10 may be placed inside a housing device, such as a tube. This housing device maintains the filter 10 in the rolled position. In an example, the housing device may be optically transparent.

Other ways of maintaining the filter 10 in the rolled position include securing the roll with tape or another suitable adhesive.

In the example shown in FIG. 1C, rolling is performed to create multiple layers $16_A$, $16_B$, $16_C$ within the filter 10. As used herein, the term layer 16 includes both the substrate 12 and the template 14', and a single layer 16 within the device 10 is measured by one 360° rotation about an axis A that aligns with the an end of the substrate 12. In the example shown in FIG. 1C, the filter 10 includes 2.5 layers, namely the outermost layer $16_A$, the middle layer $16_B$, and the centermost layer $16_C$.

As illustrated in FIG. 1C, the spacers 24 prevent the various layers $16_A$, $16_B$, $16_C$ from coming directly into contact with an adjacent layer(s) $16_A$, $16_B$, $16_C$. As such, the spacers 24 contribute to defining the space(s) 26 between the layers $16_A$, $16_B$, $16_C$. The spacers 24 may extend along the length L of the device 10, and therefore the spaces 26, which are defined between adjacent spacers 24 and between adjacent layers $16_A$, $16_B$, $16_C$, also may extend along the length L of the filter 10. The spacers 24 may also be patterned so that the formed spaces 26 have a serpentine or other pattern that optimizes desirable performance criteria, such as maximal contact between the fluid and the template 14', minimal flow resistance, or the like. Together these spaces 26 provide a fluid flow path FP that extends from one opposed end $E_1$ of the filter 10 to another opposed end $E_2$ of the filter 10. In this example then, fluid that is introduced into the filter 10 may flow along any of the spaces 26 from the fluid inlet opposed end $E_1$ to the fluid outlet opposed end $E_2$. The fluid may be introduced into the filter 10 from either of the opposed ends $E_1$ or $E_2$. However, whichever of the opposed ends $E_1$ or $E_2$ is used as a fluid inlet, it is to be understood that the other of the opposed ends $E_2$ or $E_1$ will be the fluid outlet.

Each of the opposed ends $E_1$, $E_2$ is substantially orthogonal to the surface S of the rolled substrate 12. When rolled, the surface S of the substrate 12 may also be referred to as the interior surface $S_I$ of the filter 10. This is due, at least in part, to the fact that when rolled, the surface S of the substrate 12 generally faces a center of the filter 10.

When the substrate 12 and template 14' are rolled similar to the example shown in FIG. 1C, the template 14' is the innermost portion of each layer $16_A$, $16_B$, $16_C$, and all of the molecule template locations 22, 22' are exposed to at least one of the formed spaces 26. As such, when fluid is introduced into one of the opposed ends $E_1$, $E_2$, the fluid will flow through the space(s) 26 and past the molecule template locations 22, 22'. When a molecule present in the introduced fluid finds a complementarily shaped molecule template location 22, 22' the molecule moves from the stream of fluid and attaches to the molecule template location 22, 22'.

Figure 2B:
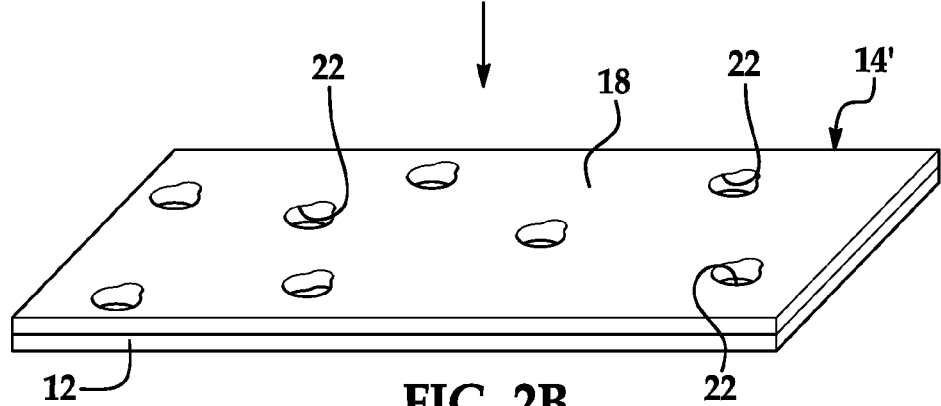
Figure 2C:
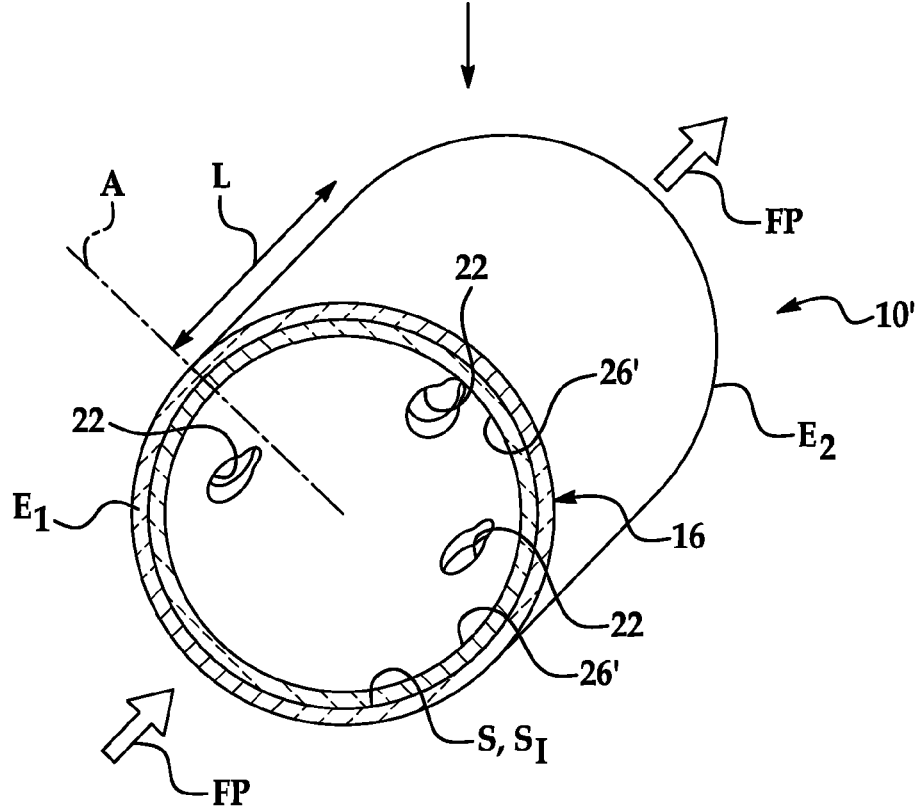

Referring now to FIGS. 2A through 2C, another example method for forming another example molecular filter 10' is depicted. Similar to FIG. 1A, FIG. 2A illustrates the substrate 12 and a pre-template 14 formed on the substrate 12. In this example, the material and thickness used for the substrate 12 enable the substrate 12 to be rolled to form a single layer 16 (shown in FIG. 2C). Any of the materials and thicknesses described in reference to the substrate 12 shown in FIG. 1A may be suitable for the substrate 12 shown in FIG. 2A.

In this example, the pre-template 14 is a precursor to the template 14' that will be formed. The pre-template 14 shown in FIG. 2A includes any desirable matrix 18 and template molecules 20, all of which are described above.

After the pre-template 14 is formed, the template molecules 20 are removed from the pre-template 14 to form the template 14', as shown in FIG. 2B. The method utilized to remove the template molecules 20 in this example may be any of the previously described template molecule removal methods. The removal of the template molecules 20 from the matrix 18 forms the molecule template locations 22 in the matrix 18, and also forms the template 14'.

Unlike the example shown in FIG. 1B, spacers 24 are not formed on the surface of the template 14' shown in FIG. 2B. In this example, the substrate 12 having the template 14' formed thereon is rolled to form a single layer 16, as shown in FIG. 2C. Since rolling in this example results in the formation of a single layer 16, spacer(s) 24 may not be desirable.

As briefly mentioned, FIG. 2C illustrates the molecular filter 10' after the substrate 12 having the template 14' thereon is rolled. As previously described, rolling may be accomplished manually or via an automated process. The molecular filter 10' may be secured in the rolled position via any suitable means, such as a device housing, or tape or another suitable adhesive.

In the example shown in FIG. 2C, rolling is performed to create the single layer 16, and to create a single space 26' extending along the length L of the filter 10'. After rolling is complete, the two ends of the substrate 12 meet or slightly overlap, and thus there is one 360° rotation about the axis A. Similar to the filter 10 shown in FIG. 1C, the fluid flow path FP in this example extends from one opposed end $E_1$ of the filter 10' to another opposed end $E_2$ of the filter 10'. However, in this example, the flow path FP is not broken up into multiple sub-paths (e.g., spaces 26 shown in FIG. 1C) via spacers 24. In this example then, fluid that is introduced into the filter 10' may flow along the single space 26' from the fluid inlet opposed end $E_1$ to the fluid outlet opposed end $E_2$. As previously described, either of the opposed ends $E_1$ or $E_2$ may function as the fluid inlet while the other of the opposed ends $E_2$ or $E_1$ functions as the fluid outlet.

Similar to the filter 10, each of the opposed ends $E_1$, $E_2$ in the filter 10' is substantially orthogonal to the surface S of the rolled substrate 12 (i.e., the interior surface $S_I$ of the device 10'). Also similar to the filter 10, when the substrate 12 and template 14' are rolled to form the filter 10', the template 14' is the innermost portion of layer 16, and all of the molecule template locations 22 are exposed to the space 26'. As such, when fluid is introduced into one of the opposed ends $E_1$, $E_2$, the fluid will flow through the space 26' and past the molecule template locations 22. When a molecule present in the introduced fluid finds a complementarily shaped molecule template location 22, the molecule moves from the stream of fluid and attaches to the molecule template location 22.

Figure 3A:
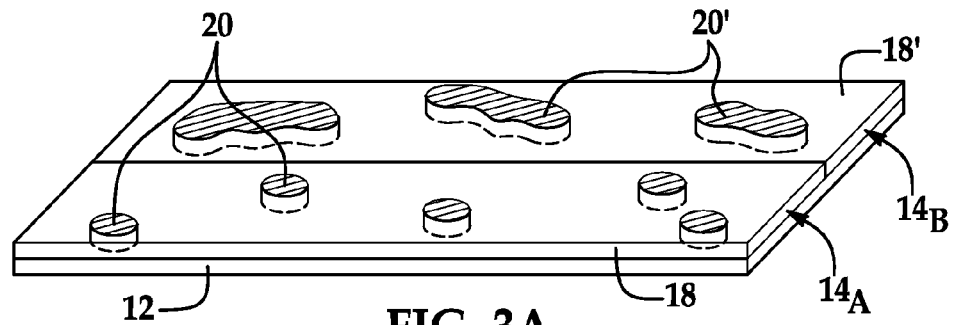
FIGS. 3A through 3C are perspective views that together illustrate the formation of an example of a molecular filter including an electrical component.
Figure 3B:
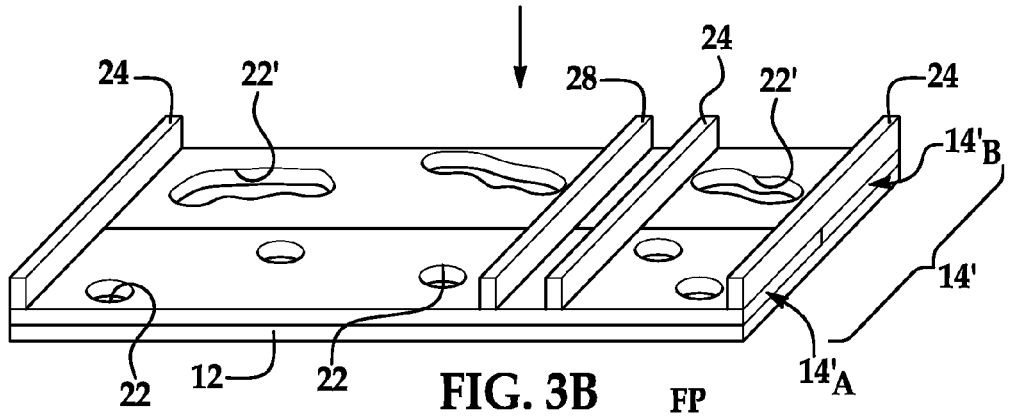
Figure 3C:
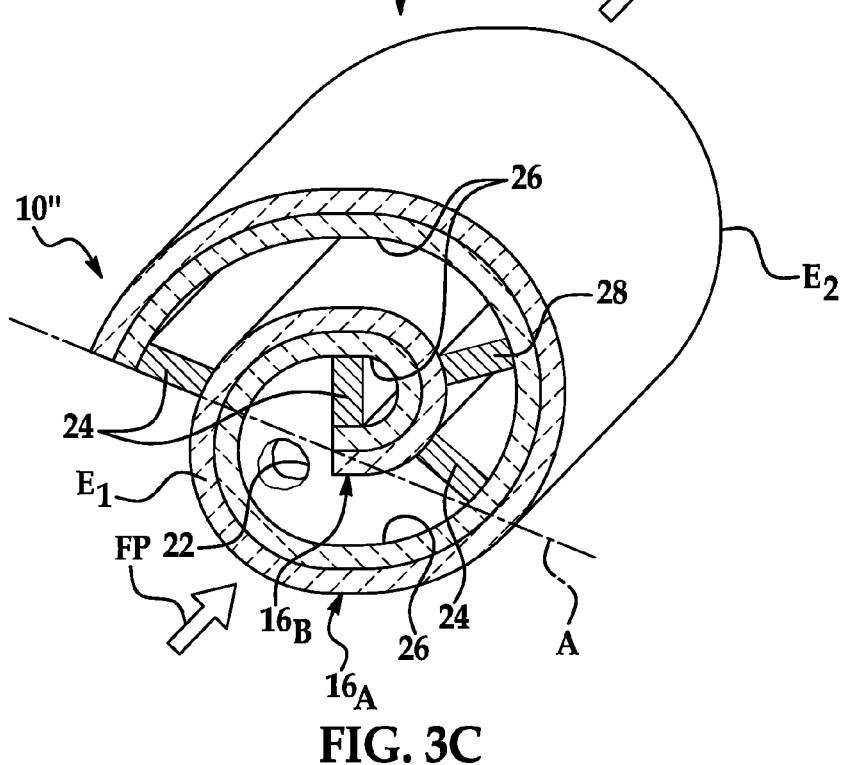

Referring now to FIGS. 3A through 3C, still another example method for forming another example molecular filter 10" is depicted. FIG. 2A illustrates the substrate 12 and two pre-templates $14_A$ and $14_B$ formed on the substrate 12. In this example, the material and thickness used for the substrate 12 enable the substrate 12 to be rolled to form a single layer 16 or to form multiple layers $16_A$, $16_B$ (shown in FIG. 3C). Any of the materials and thicknesses described in reference to the substrate 12 shown in FIG. 1A may be suitable for the substrate 12 shown in FIG. 3A.

In the example shown in FIG. 3A, two different template molecules 20, 20' are respectively mixed into two different matrices 18, 18' to form the two different pre-templates $14_A$ and $14_B$. As depicted, the template molecules 20 have a different size and/or shape than the size and/or shape of the template molecules 20'. The use of different template molecules 20, 20' enables different molecule template locations 22, 22' to ultimately be formed, which enables different molecules to be collected using a single filter 10".

The template molecules 20 are included in a matrix 18, while the template molecules 20' are included in another matrix 18'. The matrices 18 and 18' may be the same material or different materials. The respective template molecule 20, 20' and matrix 18, 18' mixtures or solutions are formed separately in this example so that the template molecules 20 can be positioned on one desirable area of the surface S of the substrate 12, and the template molecules 20' can be positioned on another desirable area of the surface S of the substrate 12. This enables a gradient of different template molecules 20, 20' to be formed along the substrate 12. In the example shown in FIG. 3A, the gradient of template molecules 20, 20' is formed along the length L of the filter 10''' that is to be formed, but it is to be understood that the gradient be formed in other directions as well. Still further, while two template molecules 20, 20' are shown, it is to be understood that any number of different template molecules 20, 20' may be utilized.

The two mixtures or solutions may be deposited simultaneously or sequentially using any of the previously mentioned techniques (e.g., printing, casting, spraying, etc.). There may or may not be some overlap and/or co-mingling at the interface between the two matrix materials 18, 18'.

The positioning of the different template molecules 20, 20' on different areas of the substrate surface S enables a gradient of template molecules locations 22, 22' to be formed (see FIG. 3B). A gradient of template molecules 20, 20' may also be formed by including all of the molecules 20, 20' in a single matrix 18 and varying the concentration of the mixture during deposition.

After the pre-templates $14_A$, $14_B$ are formed, the template molecules 20, 20' are removed from the respective pre-templates $14_A$, $14_B$ to form templates $14'_A$, $14'_B$, as shown in FIG. 3B. The method utilized to remove the template molecules 20, 20' in this example may be any of the previously described template molecule removal methods. Removal of the template molecules 20, 20' may be accomplished simultaneously, for example, if the technique selected is capable of removing the different types of template molecules 20, 20'. Alternatively, selective removal of the template molecules 20, 20' may be accomplished sequentially. For example, the pre-template $14_A$ may be masked and protected while the template molecules 20' are being removed to form the template $14'_B$; and then the template $14'_B$ may be masked and protected while the template molecules 20 are being removed to form template $14'_A$.

The removal of the template molecules 20, 20' from the respective matrices 18, 18' forms the molecule template locations 22 in the matrix 18 and the molecule template locations 22' in the matrix 18'. The removal of the template molecules 20, 20' also forms the template 14', which includes both template $14'_B$ and template $14'_A$.

Depending upon whether a single layer 16 is to be formed or multiple layers $16_A$, $16_B$ are to be formed, spacers 24 may not or may be formed on the template 14'. In the example shown in FIG. 3C, the substrate 12 having the template 14' thereon is rolled to form multiple layers $16_A$ and $16_B$, and thus spacers 24 are formed on the template 14' surface. As previously described in reference to FIG. 1C, when the substrate 12 having the template 14' thereon is rolled, the spacers 24 will form fluid flow path spaces 26 and will keep the layers $16_A$ and $16_B$ from coming into direct contact with one another.

As shown in FIG. 3B, one or more electrodes 28 may also be formed on the template 14'. The introduction of electrode(s) 28 into the filter 10''' may be desirable when the filter 10''' will be used in electrochemical sensing or optical and electrochemical sensing. The electrode(s) 28 may also be formed directly on the surface S of the substrate 12 and the template 14' may be formed thereon (see FIGS. 5A and 5B). In the latter example, the template 14' may be formed so that the matrix 18 and/or 18' contacts the electrode(s) 28 and also covers the electrode(s) 28.

Figure 4:
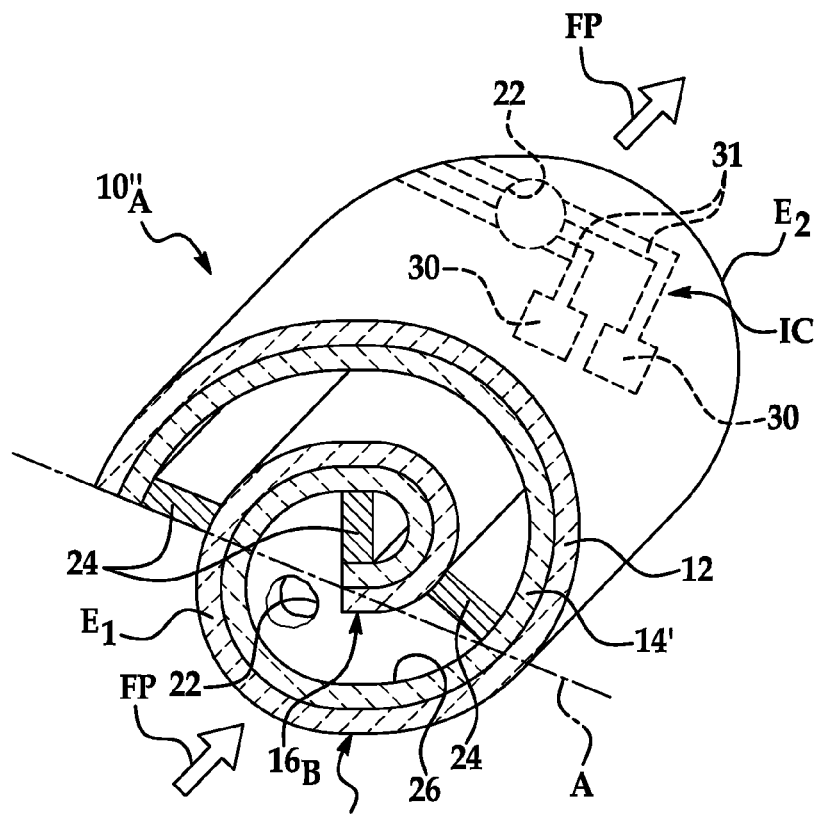
FIG. 4 illustrates a perspective view of another example of a molecular filter including multiple electrical components.

In an example, the electrode(s) 28 is/are deposited to extend the entire length L of the filter 10''' when the substrate 12 having the template 14' thereon is rolled. In another example, the electrode(s) 18 is/are deposited to extend from one of the opposed ends $E_1$ or $E_2$ into the filter 10''' along a portion of the length L. In still another example, the electrode(s) material may also be deposited in a desirable pattern to form an integrated circuit within the ultimately formed filter 10'''. An example of a filter $10_A'''$ having an integrated circuit IC formed therein is shown in FIG. 4. In the example shown in FIG. 4, the integrated circuit IC is shown in dashed lines, at least in part because the integrated circuit IC is formed under or on the template 14' and thus is inside of the filter $10_A'''$ after the substrate 12 having the template 14' thereon is rolled. This example integrated circuit IC includes the electrode material deposited and patterned to form contact pads 30 and electrical traces 31 for signal conduction. As illustrated, the traces 31 electrically connect to the molecule template location(s) 22. Alternatively, the dashed lines shown in FIG. 4 may be electrodes 28 (e.g., gold electrodes) that may be connected to voltage/current sources to apply electrical forces to any charged species in the introduced fluid and to sense such species. The electrode(s) 28 or electrode material making up the components (e.g., 30 and 31) of the integrated circuit IC may be deposited using any suitable technique, such as photolithography, electron beam lithography screen printing, flex-circuit board patterning, or the like.

Suitable materials for the electrode(s) 28, contact pads 30, and/or traces 31 include any conductive or semi-conductive material, such as gold, platinum, aluminum, silver, tungsten, copper, silicon, germanium, III-V compound semiconductors (e.g., GaAs, InP), etc. In an example, the electrode(s) 28 are formed as single walled nanotubes. The electrode(s) 28 (or other electrical components) may be formed as a single layer (as shown in FIG. 3B) of one of the listed materials, or the electrode(s) 28 (or other electrical components) may be formed as multi-layered structures including conductive or semi-conductive electrode material layers separated by insulator material layers (similar to flexible and rigid circuit boards).

The dimensions of the electrode(s) 28 (or other electrical components) will depend, at least in part, on the dimensions of the substrate 12, the thickness of the matrix 18, 18', and/or whether the filter 10''' includes a single layer 16 or multiple layers $16_A$, $16_B$ when rolled. In an example, the height and/or width of the electrode(s) 28 (or other electrical components) ranges from about 10 nm to about 100 nm. Furthermore, although the electrode 28 is shown with a rectangular cross-section, the electrode(s) 28 may also have a square, a circular, an elliptical, or a more complex cross-section.

Referring now to FIG. 3C, the substrate 12 having the template 14' thereon that is shown in FIG. 3B has been rolled, and the molecular filter 10''' is depicted. As previously described, rolling may be accomplished manually or via an automated process, and securing of the roll may be accomplished via any suitable means.

In the example shown in FIG. 3C, the electrode(s) 28 is/are present inside of the filter 10''' after rolling. This enables electrical signals to be spiraled into the center of the filter 10''' in some instances, and through the length L of the filter 10''' in some other instances.

In the example shown in FIG. 3C, rolling is performed to create the layers $16_A$ and $16_B$ and to create the spaces 26 extending along the length L of the filter 10". As illustrated in FIG. 3C, the spacers 24 prevent the various layers 16$_A$, 16$_B$, from coming directly into contact with each other, and contribute to defining the spaces 26 between the layers 16$_A$, 16$_B$. Together these spaces 26 provide a fluid flow path FP that extends from one opposed end E$_1$ of the filter 10" to another opposed end E$_2$ of the filter 10". While the spacers 24 extend straight along the length L of the filter 10", it is to be understood that the spacers 24 may also be patterned so that the formed spaces 26 have a serpentine or other desirable pattern. In this example then, fluid that is introduced into the filter 10" may flow along any of the spaces 26 from the fluid inlet opposed end E$_1$ to the fluid outlet opposed end E$_2$. The fluid may be introduced into the filter 10" from either of the opposed ends E$_1$ or E$_2$. However, whichever of the opposed ends E$_1$ or E$_2$ is used as a fluid inlet, it is to be understood that the other of the opposed ends E$_2$ or E$_1$ will be the fluid outlet.

As in the other examples disclosed herein, each of the opposed ends E$_1$, E$_2$ is substantially orthogonal to the surface S of the rolled substrate 12, or the interior surface S$_I$ of the filter 10".

When the substrate 12 and template 14' are rolled similar to the example shown in FIG. 3C, the template 14' (including templates 14'$_A$ and 14'$_B$) is the innermost portion of each layer 16$_A$, 16$_B$, and all of the molecule template locations 22, 22' are exposed to at least one of the formed spaces 26. The rolled filter 10" has the gradient of template molecules locations 22, 22' along the length L of the filter 10". In other words, different functionality has been introduced along the length L of the filter 10". In this particular example, the molecule template locations 22 are located near the end E$_1$ and the molecule template locations 22' are located near the end E$_2$. This gradient enables different molecules to be collected/filtered at different areas along the length L of the filter 10". In an example, the molecule template locations 22 may be designed to attract undesirable molecules that may potentially compete with molecules of interest for the locations 22'. The ability to incorporate different template molecules 20, 22 and form different molecule template locations 22' increases the control over chemical, temporal, and other characteristics of the filters 10, 10', 10" disclosed herein.

When fluid is introduced into one of the opposed ends E$_1$, E$_2$ of the filter 10" shown in FIG. 3C, the fluid will flow through the space(s) 26 and past the molecule template locations 22, 22'. When a molecule present in the introduced fluid finds a complementarily shaped molecule template location 22, the molecule moves from the stream of fluid and attaches to the molecule template location 22. Similarly, when a molecule present in the introduced fluid finds a complementarily shaped molecule template location 22', the molecule moves from the stream of fluid and attaches to the molecule template location 22'.

Figure 5A:
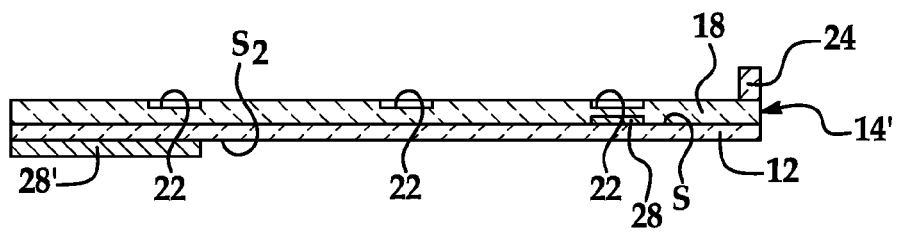
FIGS. 5A and 5B illustrate cross-sectional views illustrating the formation of yet another example of a molecular filter, where FIG. 5B also illustrates an electrical system including the molecular filter.
Figure 5B:
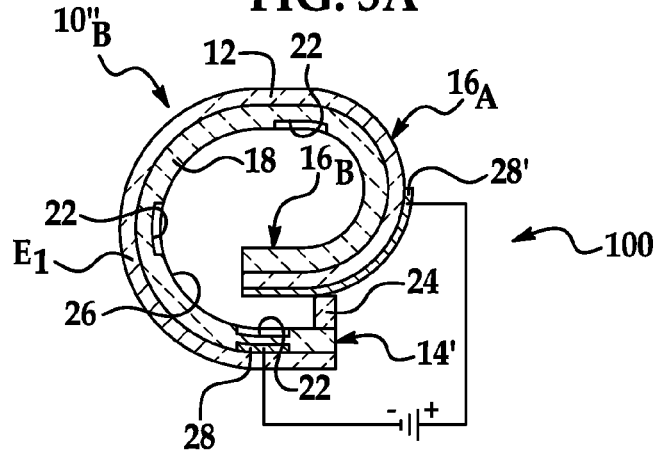

Referring now to FIGS. 5A and 5B, still another example of forming another example molecular filter 10$_B$" is depicted. This molecular filter 10$_B$" is similar to the molecular filters 10" and 10$_A$ at least because it includes electrical components (e.g., electrodes 28 and 28').

FIG. 5A illustrates the substrate 12 and a template 14' formed thereon. In this example, the material and thickness used for the substrate 12 enable the substrate 12 to be rolled to form any desirable number of layer(s) 16 (e.g., 1.25 layers). Any of the materials and thicknesses described in reference to the substrate 12 shown in FIG. 1A may be suitable for the substrate 12 shown in FIG. 5A.

In this example, an electrode 28 is formed on the surface S of the substrate 12. The electrode 28 may be formed prior to deposition of the mixture or solution containing the matrix 18 and the template molecules 20 (not shown in FIGS. 5A and 5B) and prior to removal of the template molecules 20 to form the template 14' with the molecule template locations 22. The electrode 28 may be formed using the methods and materials previously described, except that the electrode material is deposited on the substrate surface S rather than on the template 14' surface. Once the electrode 28 is formed on the surface S, the template 14' may be formed. The template 14' may be formed via any of the methods described herein. As an example, the mixture or solution including the matrix 18 and the template molecules 20 may be deposited to partially or completely cover the electrode 28. As shown in FIG. 5A, the mixture or solution including the matrix 18 and the template molecules 20 is deposited to completely cover the electrode 28 except at the ends E$_1$, E$_2$ of the rolled filter 10$_B$" shown in FIG. 5B. After removal of the template molecules 20, the template 14' is formed over the electrode 28'.

As shown in FIG. 5A, this example also includes an electrode 28' established on the opposed surface S$_2$ of the substrate 12. The electrode 28' may be any of the materials set forth herein for electrode 28, and may be formed via any of the methods set forth herein for forming electrode 28. In some examples, the electrode 28' is positioned on the opposed surface S$_2$ such that when the substrate 12 having the template 14' thereon is rolled, the electrode 28' at least partially aligns with the electrode 28. In an example, the electrode 28' may be positioned so that when the substrate 12 is rolled, the electrode 28' is parallel to the electrode 28, but is positioned across a space 26 from the electrode 28. While not shown, it is to be understood that in this example, the electrode 28' extends along all or a portion of the length L of the filter 10$_B$" in the same manner as the electrode 28. In the example shown in FIGS. 5A and 5B, the electrode 28' is positioned so that when the substrate 12 is rolled, the electrode 28' is perpendicular to the electrode 28, and is positioned across a space 26 from the electrode 28. In this example, the electrodes 28, 28' partially overlap in an area so that they form a parallel capacitor capable of providing a large uniform field region within the overlap region.

In another example, electrodes 28 and 28' may be positioned side by side on the surface S of the substrate 12 such that they are within from about 1 μm to about 100 μm of one another. When voltages are applied to such side-by-side electrodes 28, 28' in the rolled filter, the fluid within the filter is subjected to a field gradient. In this and the previously described examples of the electrodes 28 and 28', voltages applied to the electrodes 28 and 28' may be used to move fluid molecular components in a desirable manner depending upon their charge configuration (e.g., towards or away from molecule template locations 22, 22'). Depending upon whether a single layer 16 is to be formed or multiple layers 16$_A$, 16$_B$ are to be formed, spacers 24 may not or may be formed on the template 14'. In the example shown in FIG. 5B, the substrate 12 having the template 14' thereon is rolled to form a first layer 16$_A$ and part of a second layer 16$_B$, and thus spacer 24 is formed on the template 14' surface. As previously described in reference to FIG. 1C, when the substrate 12 having the template 14' thereon is rolled, the spacer(s) 24 will assist in forming fluid flow path space(s) 26 and will keep the layers 16$_A$ and 16$_B$ from coming into direct contact with one another.

In FIG. 5B, the substrate 12 having the template 14' thereon (that is shown in FIG. 5A) has been rolled, and the molecular filter 10$_B$" is depicted. As previously described, rolling may be accomplished manually or via an automated process, and securing of the roll may be accomplished via any suitable means.

The filter 10$_B$" is shown as part of an electrical sensing system 100. The electrode 28 is in electrical contact with the template 14' and may be operatively and electrically connected to the electrode 28' via electrical components that allow current to flow between the electrodes 28, 28'. Other electrical components that are not shown may be electrically and operatively connected to the electrodes 28, 28'. Examples of these other electrical components enable the detection of a change in impedance, resistance, conductance, voltage, or the like during operation of the system 100.

During operation of the system 100, a fluid (i.e., a liquid (e.g., water, ethanol, etc.) or gas (e.g., air, nitrogen, argon, etc.) containing or acting as a carrier for the molecules is introduced into the opposed end $E_1$. The respective molecules may attach to a respective one of the molecule template locations 22. The electrode(s) 28, 28' and the other electrical components achieve effective signal conversion of molecule binding (i.e., molecule attachment to the molecule template location(s) 22, 22') to a measurable electrical signal. For example, when the molecule template locations 22, 22' are unoccupied, the molecule template locations 22, 22' create conductive paths for current to flow from the fluid into the electrode (e.g., electrode 28). However, when a molecule resides in the molecule template locations 22, 22', its presence impedes the flow of charge, thereby increasing the resistance. This increase in resistance may be detected and utilized to identify the captured molecule.

Figure 6A:
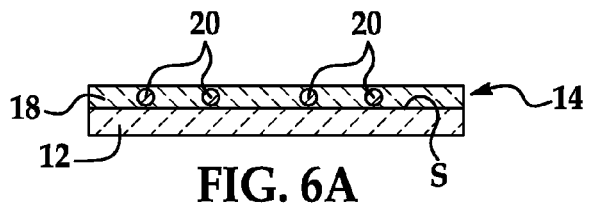
FIGS. 6A through 6E are cross-sectional views that together illustrate the formation of still another example of a molecular filter.
Figure 6B:
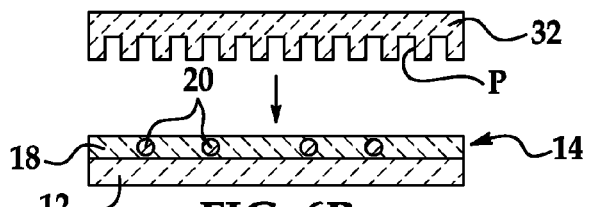
Figure 6C:
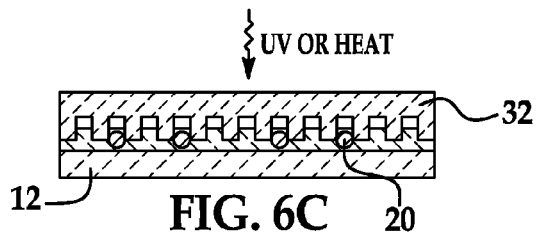
Figure 6D:
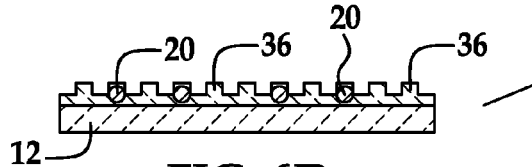
Figure 6E:
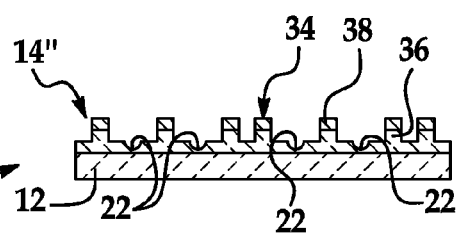

Referring now to FIGS. 6A through 6E, another method is shown which integrates optical signal amplifying structures 34 into another example of the template 14", which is shown in FIG. 6E. FIG. 6A illustrates a cross-sectional view of the substrate 12 having the pre-template 14 formed thereon.

FIG. 6B also illustrates a mold 32 that may be used to imprint optical signal amplifying structures 34 into the matrix 18. The mold 32 may be formed of single crystalline silicon, polymeric materials (acrylics, polycarbonates, polydimethylsiloxane (PDMS), polyimide, etc.), metals (aluminum, copper, stainless steel, nickel, alloys, etc.), quartz, ceramic, sapphire, silicon nitride, or glass.

The mold 32 includes a pattern P for the base portion 36 of the optical signal amplifying structures 34. The pattern P is a negative replica of the desired base portion 36, and thus defines the shapes for the base portions(s) 36 of the optical signal amplifying structures 34 that are to be formed. The pattern P may be a negative replica of any nano-structures, which have at least one dimension ranging from about 1 nm to about 100 nm. Examples of nano-structures include antennas, pillars or nano-wires, poles, flexible columnar or finger-like structures, cone-shaped structures, multi-faceted structures, etc. When more than one optical signal amplifying structure 34 is desired, the pattern P for the base portions 36 may all be the same (e.g., all pillars), may all be different (e.g., one pillar, one pole, one finger-like structure, etc.), or the pattern P for some base portions 36 may be different from one or more other base portions 36 (e.g., one pillar, two poles, two cones, etc.). Furthermore, when more than one signal amplifying structure 34 is desired, the pattern P for the base portions 36 may have the same or different dimensions.

The pattern P may be integrally formed in the mold 32. In an example, the pattern P may be formed in the mold 32 via deep reactive ion etching and passivation to form, for example, nanocone shaped base portions 36. More specifically, the Bosch process may be used, and this process involves a series of alternating cycles of etching (e.g., using $SF_6$ and $O_2$ plasmas) and passivation (e.g., using a $C_4F_8$ plasma). The morphology of the resulting pattern P may be controlled by controlling the conditions (e.g., vacuum pressure, RF power, total processing time, individual etching cycle time, individual passivation cycle time, and gas flow rates) of the process. In an example, the etcher may be operated at a pressure of 15 mTorr, the coil and platen powers of the etcher are 800 W and 10 W, respectively, each etching cycle (with $SF_6$ and $O_2$) is 6 seconds, each passivation cycle (with $C_4F_8$) is 5 seconds, and the flow rates for $SF_6$, $O_2$, and $C_4F_8$ are 100 sccm, 13 sccm, and 100 sccm, respectively. More generally, the flow rate may be any rate up to about 100 sccm.

The pattern P that forms the base portions 36 may include a regular or non-regular array. The etching and passivation process previously described often results in a non-regular array. It is to be understood that in order to generate a regular array, a fabrication method, such as focused ion-beam, e-beam lithography, or optical lithography may be used to fabricate the mold 32. It is believed that the pattern P may be designed in a predetermined manner to enable the resulting base portions to be sensitive to a targeted range, for example, on the Raman spectrum (e.g., capable of producing stronger signals in a particular wavelength) or on another optical sensing spectrum.

As shown in FIG. 6C, the mold 32 is pressed into the matrix 18 having the template molecules 20 mixed therewith. In this example, the matrix 18 may be an ultraviolet (UV) curable resist material or a thermally curable resist material that also acts as a suitable molecule trapping material. When the mold 32 is pressed into the matrix 18, it is to be understood that the template molecules 20 may be shifted as a result of coming into contact with the mold 32.

While the mold 28 is pressed into the matrix 18, the structure may be exposed to UV light or heat in order to cure the matrix 18. This is shown in FIG. 6C. It is to be understood that the time for UV or heat exposure, the power of the UV lamp used, the temperature of the heat, and other like curing parameters will depend, at least in part, on the matrix material 18 that is used. Once curing is complete, the mold 32 may be removed (shown in FIG. 6D), and the resulting structure includes the cured matrix 18 patterned to form the base portions 26 of the optical signal amplifying structure(s) 34.

Once the matrix 18 is patterned, the template molecules 20 may be removed via any of the removal methods described herein to form the template 14", shown in FIG. 6E. The removal of the template molecules 20 exposes the molecule template locations 22.

Before or after the template molecules 20 are removed, the method in this example may include selectively depositing a signal-enhancing material 38 on a surface of the base portion 36 to form the signal amplifying structures 34. The signal-enhancing material 38 is capable of enhancing an optical signal that is generated during a particular sensing process. In an example, the signal-enhancing material 38 is a Raman signal-enhancing material that increases the number of Raman scattered photons when the molecule (or other species of interest) is located within the molecule template location 22 and proximate to the signal amplifying structure(s) 34, and when the molecule and material 38 are subjected to light/electromagnetic radiation. Raman signal-enhancing materials include, but are not limited to, silver, gold, and copper.

The signal-enhancing material 38 may be established by any suitable selective deposition or other selective coating technique. In examples, the selective deposition technique may be used so that the material 38 is established on, for example, the tips or top surfaces of the bases 36 alone. As examples, the material 38 may be deposited via electron-beam (e-beam) evaporation or sputtering. As other examples, the signal-enhancing material 38 may be pre-formed nanoparticles (e.g., of silver, gold, copper, etc.), which are selectively coated onto the base portions 36. Such nanoparticles may have an average diameter ranging from about 1 nm to about 10 nm. It is believed that the presence of the signal-enhancing material 38 nanoparticles at the apex or top surface of the bases 36 further enhances the electric field during, e.g., a SERS operation. The material 38 itself may also have a surface roughness that spontaneously forms during the deposition process. This surface roughness can act as additional optical antennas to increases the SERS-active sites over each signal amplifying structure(s) 34.

Together the molecule template locations 22 formed in the matrix 18 and the signal amplifying structure(s) 34 form the template 14", shown in FIG. 6E. The substrate 12 having the template 14" formed therein may be rolled as previously described to form a filter having a single layer 16 and a space 26' or multiple layers $16_A$, $16_B$, $16_C$, etc. and spaces 26. The filter formed with this example template 14" may be particularly suitable for use in an optical sensing application.

In any of the examples of the filters 10, 10', 10", $10_A$", $10_B$" disclosed herein, it is to be understood that the substrate 12 and template 14' may have holes 23 formed therein. Example holes 23 are shown in the filter 10 of FIG. 1C. These holes 23 would permit fluid to flow radially outward and/or inward to promote flow through the filters 10, 10', 10", $10_A$", $10_B$" and between spaces 26, 26'. It is to be understood that radial flow may be utilized in addition to lateral flow from one end $E_1$ to the other end $E_2$. Radial flow permits fluid flow within the filter 10, 10', 10", $10_A$", $10_B$" and not just through the filter 10, 10', 10", $10_A$", $10_B$".

Also in any of the examples disclosed herein, the length L and diameter of the filters 10, 10', 10", $10_A$", $10_B$" may be adjusted to ensure that a desirable amount of the introduced fluid comes into contact with the molecule template locations 22, 22' for an appropriate contact time interval.

Figure 7:
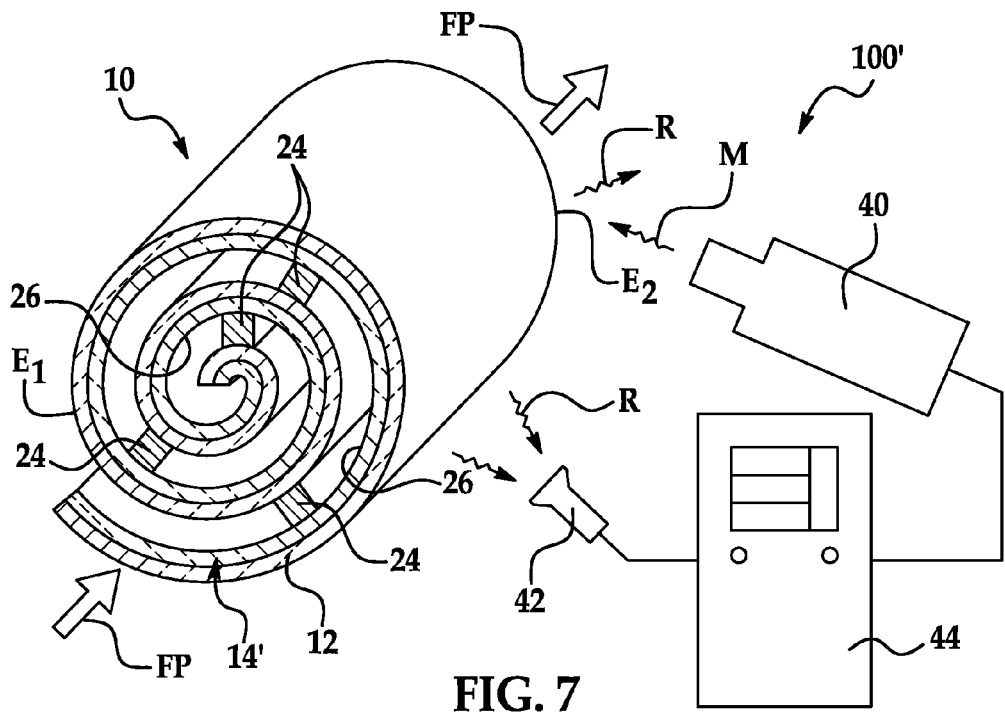
FIG. 7 is a schematic illustration of a Raman spectroscopy system including an example of a molecular filter.

Referring now to FIG. 7, an example of an optical sensing system 100' is depicted. The system 100' shown in FIG. 7 is a Raman spectroscopy system that includes a laser source 40, an example of the molecular filter 10 (although filters 10', 10", $10_A$", $10_B$" may also be utilized in the optical sensing system 100' if the substrate 12 and matrix 18 are optically transparent), and a photodetector 42. While a Raman spectroscopy system is shown, it is to be understood that the molecular filters 10, 10', 10", $10_A$", or $10_B$" may be used in other optical sensing systems based upon, for example, fluorescence.

The laser source 40 may be a light source that has a narrow spectral line width, and is selected to emit monochromatic light beams M within the visible range or within the near-infrared range. When the sensing system 100' is based upon fluorescence, the laser source 40 may be selected to emit monochromatic light beams M within the ultraviolet to visible range. The laser source 40 may be selected from a continuous wave laser or a pulsed laser. The laser source 40 is positioned to project the light M through the substrate 12 and matrix 18 onto the molecules captured in the molecule template locations 22, 22'. A lens (not shown) and/or other optical equipment (e.g., optical microscope) may be used to direct (e.g., bend) the laser light M in a desired manner. In one example, the laser source 36 is integrated on a chip. The laser source 40 may also be operatively connected to a power supply (not shown).

During operation of the system 100', a fluid (i.e., a liquid (e.g., water, ethanol, etc.) or gas (e.g., air, nitrogen, argon, etc.) containing or acting as a carrier for the molecules is introduced into the opposed end $E_1$. The respective molecules may attach to a respective one of the molecule template locations 22.

The laser source 40 is then operated to emit light M toward the molecular filter 10. The molecules positioned within the molecule template locations 22 of the molecular filter 10 interact with and scatter the light/electromagnetic radiation M (note that the scattered light/electromagnetic radiation is labeled R). The Raman scattered radiation R is redirected toward the photodetector 42, which may optically filter out any reflected components and/or Rayleigh components and then detect an intensity of the Raman scattered radiation R for each wavelength near the incident wavelength.

While not shown, the system 100' may include a light filtering element positioned between the molecular filter 10 and the photodetector 42. This light filtering element may be used to optically filter out any Rayleigh components, and/or any of the Raman scattered radiation R that is not of a desired region. It is to be understood that the system 100' may also include a light dispersion element (not shown) positioned between the molecular filter 10 and the photodetector 42. The light dispersion element may cause the Raman scattered radiation R to be dispersed at different angles. The light filtering element and the light dispersion element may be part of the same device or may be separate devices.

As shown in FIG. 7, a processor 44 may be operatively connected to both the laser source 40 and the photodetector 42 to control both of these components 40, 42. The processor 44 may also receive readings from the photodetector 42 to produce a Raman spectrum readout, the peaks and valleys of which are then utilized for analyzing the analyte molecules.

In any of the examples disclosed herein, it is believed that the filters 10, 10', 10", $10_A$", $10_B$" and a filter formed using the substrate 12 and template 14" may each be unrolled and cleaned to remove any captured molecules and any remaining fluid. The substrate 12 and template 14', 14" formed thereon may then be re-rolled for use as a filter in another sensing application. As such, the examples of the filters disclosed herein are reusable.

The templates 14', 14" and filters 10, 10', 10", $10_A$", $10_B$" may advantageously be formed without complicated reactant chemistry and without delicate chemicals that are sensitive to minor changes in the environment. The templates 14, 14' disclosed herein may be specifically designed to be selective towards one molecule or towards a large class of molecules, depending, at least in part, upon the sensing application that is desired.

It is to be understood that the ranges provided herein include the stated range and any value or sub-range within the stated range. For example, a range from about 2 μm to about 250 μm should be interpreted to include not only the explicitly recited limits of about 2 μm to about 250 μm, but also to include individual values, such as 4.5 μm, 125 μm, 200 μm, etc., and sub-ranges, such as from about 15 μm to about 100 μm, from about 100 μm to about 200 μm, etc. Furthermore, when "about" is utilized to describe a value, this is meant to encompass minor variations (up to +/−10%) from the stated value.

While several examples have been described in detail, it will be apparent to those skilled in the art that the disclosed examples may be modified. Therefore, the foregoing description is to be considered non-limiting.

What is claimed is:
1. A molecular filter, comprising:
a rolled substrate having an interior surface and opposed ends that are substantially orthogonal to the interior surface, the rolled substrate defining a layer and a fluid flow path extending from one of the opposed ends to an other of the opposed ends; and a template positioned on the interior surface of the rolled substrate, the template including:
  a matrix selected from a polymer matrix and a host molecule matrix; and
  molecule template locations formed in the matrix;
wherein:
  the filter is to be used in an optical system; and
  the rolled substrate is an optically transparent material.

2. The molecular filter as defined in claim 1 wherein the rolled substrate defines a plurality of layers, and wherein the molecular filter further comprises a spacer positioned on the template, the spacer to further define the plurality of layers and the fluid flow path.

3. The molecular filter as defined in claim 1 wherein the molecule template locations are varied at least once along a length of the molecular filter that extends from the one of the opposed ends of the rolled substrate to the other of the opposed ends of the rolled substrate.

4. The molecular filter as defined in claim 1 wherein the rolled substrate is selected from polyimide, poly(ethylene terephthalate), poly(ethylene 2,6-naphthalate), stainless steel, biocompatible silicate-collagen hybrid fibril sheets, biocompatible silicone rubber based on poly(methylhydrogensiloxane-co-dimethylsiloxane), graphene oxide-based sheets, bio-functionalized graphene, and substrates with patterned cell signaling proteins.

5. The molecular filter as defined in claim 1 wherein the matrix is a host molecule matrix.

6. A method for making the molecular filter as defined in claim 1, the method comprising:
  forming the molecule template locations by:
    coating a combination of template molecules and the matrix onto the interior surface of the substrate; and
    removing the template molecules, thereby forming the molecule template locations in the matrix; and
  rolling the substrate formed from the optically transparent material such that i) the surface having the template thereon becomes the interior surface of the rolled substrate, and ii) the opposed ends of the substrate are formed that are substantially orthogonal to the interior surface.

7. A molecular filter, comprising:
  a rolled substrate having an interior surface and opposed ends that are substantially orthogonal to the interior surface, the rolled substrate defining a layer and a fluid flow path extending from one of the opposed ends to an other of the opposed ends; and
  a template positioned on the interior surface of the rolled substrate, the template including:
    a matrix selected from a polymer matrix and a host molecule matrix; and
    molecule template locations formed in the matrix;
  wherein:
    the filter is to be used in an electrical system; and
    the filter further comprises an electrode positioned on the interior surface of the rolled substrate and in contact with the template or on the surface of the template, the electrode extending from at least one of the opposed ends.

8. The molecular filter as defined in claim 7 wherein the rolled substrate defines a plurality of layers, and wherein the molecular filter further comprises a spacer positioned on the template, the spacer to further define the plurality of layers and the fluid flow path.

9. The molecular filter as defined in claim 7 wherein the molecule template locations are varied at least once along a length of the molecular filter that extends from the one of the opposed ends of the rolled substrate to the other of the opposed ends of the rolled substrate.

10. The molecular filter as defined in claim 7 wherein the rolled substrate is selected from polyimide, poly(ethylene terephthalate), poly(ethylene 2,6-naphthalate), stainless steel, biocompatible silicate-collagen hybrid fibril sheets, biocompatible silicone rubber based on poly(methylhydrogensiloxane-co-dimethylsiloxane), graphene oxide-based sheets, bio-functionalized graphene, and substrates with patterned cell signaling proteins.

11. The molecular filter as defined in claim 7 wherein the matrix is a host molecule matrix.

12. A method for making the molecular filter as defined in claim 7, the method comprising:
  forming the molecule template locations by:
    coating a combination of template molecules and the matrix onto the interior surface of the substrate; and
    removing the template molecules, thereby forming the molecule template locations in the matrix;
  forming a plurality of spacers on the template such that the spacers respectively define a plurality of the layers and the fluid flow path extending from one of the opposed ends to the other of the opposed ends when the substrate is rolled;
  forming the electrode on the surface of the substrate and in contact with the template such that the electrode extends from at least one of the opposed ends when the substrate is rolled; and
  rolling the substrate such that i) the surface having the template thereon becomes the interior surface of the rolled substrate, and ii) the opposed ends of the substrate are formed that are substantially orthogonal to the interior surface.

13. A molecular filter, comprising:
  a rolled substrate having an interior surface and opposed ends that are substantially orthogonal to the interior surface, the rolled substrate defining a layer and a fluid flow path extending from one of the opposed ends to an other of the opposed ends; and
  a template positioned on the interior surface of the rolled substrate, the template including:
    a matrix selected from a polymer matrix and a host molecule matrix; and
    molecule template locations formed in the matrix;
  wherein the template further comprises an optical signal amplifying structure imprinted into the matrix.

14. A method for making the molecular filter as defined in claim 13, the method comprising:
  forming the molecule template locations by:
    coating a combination of template molecules and the matrix onto the interior surface of the substrate; and
    removing the template molecules, thereby forming the molecule template locations in the matrix;
  nano-imprinting the template to form the optical signal amplifying structure in the matrix material;
  coating a signal enhancing material on the optical signal amplifying structure; and
  rolling the substrate such that i) the surface having the template thereon becomes the interior surface of the rolled substrate, and ii) the opposed ends of the substrate are formed that are substantially orthogonal to the interior surface.

15. A molecular sensing system, comprising:
  a molecular filter, including:
    a rolled substrate having an interior surface and opposed ends that are substantially orthogonal to the interior surface, the rolled substrate defining a plurality of layers and a fluid flow path extending from one of the opposed ends to an other of the opposed ends; and a template positioned on the interior surface of the rolled substrate, the template including:
- a matrix selected from a polymer matrix and a host molecule matrix; and
- molecule template locations formed in the matrix; and a molecular sensing device including any of i) an electrical component incorporated into the molecular filter to electrically detect a signal generated in response to a molecule being trapped in at least one of the molecule template locations, or ii) an optical component operatively positioned with respect to the molecular filter to optically detect a signal generated in response to a molecule being trapped in at least one of the molecule template locations.

16. The molecular sensing system as defined in claim 15 wherein the optical component is a detector, and wherein the system further comprises a light source chosen from an ultraviolet light source, a visible light source, and an infrared light source.

17. The molecular sensing system as defined in claim 15, further comprising a processor operatively connected to the any of i) the electrical component, or ii) the optical component.

* * * * *